(12) United States Patent  
Wandel (10) Patent No.: US 9,066,722 B2  
(45) Date of Patent: Jun. 30, 2015

(54) INSTRUMENT FOR FUSING AND SEVERING TISSUE

(71) Applicant: ERBE Elektromedizin GmbH, Tuebingen (DE)

(72) Inventor: Waldemar Wandel, Kusterdingen (DE)

(73) Assignee: ERBE ELEKTROMEDIZIN GMBH, Tuebingen (DE)

( * ) Notice: Subject to any disclaimer, the term of this patent is extended or adjusted under 35 U.S.C. 154(b) by 68 days.

(21) Appl. No.: 13/917,208

(22) Filed: Jun. 13, 2013

(65) Prior Publication Data

US 2013/0345702 A1 Dec. 26, 2013

(30) Foreign Application Priority Data

Jun. 25, 2012 (EP) .................................... 12173329

(51) Int. Cl.
*A61B 18/12* (2006.01)
*A61B 18/14* (2006.01)
*A61B 18/00* (2006.01)

(52) U.S. Cl.
CPC ... *A61B 18/1445* (2013.01); *A61B 2018/00184* (2013.01); *A61B 2018/1455* (2013.01)

(58) Field of Classification Search
CPC .......... A61B 18/1442; A61B 18/1445; A61B 2018/00184; A61B 2018/1455; A61B 2018/0063; A61B 2018/00601; A61B 2018/00404; A61B 17/285
USPC ..................................................... 606/51–52
See application file for complete search history.

(56) References Cited

U.S. PATENT DOCUMENTS

| 2003/0018332 | A1* | 1/2003 | Schmaltz et al. ............... 606/51 |
| 2003/0199869 | A1 | 10/2003 | Johnson et al. |
| 2006/0074417 | A1* | 4/2006 | Cunningham et al. .......... 606/51 |
| 2006/0079891 | A1* | 4/2006 | Arts et al. ........................ 606/51 |
| 2008/0021450 | A1* | 1/2008 | Couture .......................... 606/51 |

(Continued)

FOREIGN PATENT DOCUMENTS

| DE | 202007009165 | 8/2007 |
| DE | 60226015 | 6/2009 |

(Continued)

OTHER PUBLICATIONS

European Search Report, related Application No. EP 12173329, Nov. 20, 2012, 7 pages.
Chinese office action in corresponding Chinese application No. 2013102518576, dated Jan. 7, 2015, 13 pages.

*Primary Examiner* — Michael Peffley
*Assistant Examiner* — Daniel Fowler
(74) *Attorney, Agent, or Firm* — Fitch, Even, Tabin & Flannery LLP (57) ABSTRACT

An instrument (10) for fusing and severing vessels in accordance with the invention comprises a first branch (19) with a first electrode (33) and a second branch 20 that is supported so as to be movable toward and away from the first electrode (33), wherein the second branch (20) has a longitudinal slit (31). A knife (21) is arranged in said slit so as to be movable longitudinally relative to the shaft (11). The knife (21) is associated with a vertical adjustment mechanism (54) for adjusting the knife (21) perpendicularly to the longitudinal movement as a function of the longitudinal movement of said knife. As a result of this, a premature dulling of the tip (28*b*) or the sliding edge (28*a*) of the knife 21 due to contact with the ceramic base body (23) or the edges or the step (55) is avoided.

20 Claims, 4 Drawing Sheets

(56) References Cited

U.S. PATENT DOCUMENTS

| | | |
|---|---|---|
| 2009/0043305 A1 | 2/2009 | Brodbeck et al. |
| 2009/0326531 A1 | 12/2009 | Geiselhart |
| 2011/0054468 A1 | 3/2011 | Dycus |
| 2012/0095460 A1 | 4/2012 | Rooks et al. |

FOREIGN PATENT DOCUMENTS

| | | |
|---|---|---|
| WO | 02080795 | 10/2002 |
| WO | 2006021269 | 3/2006 |
| WO | 2008040483 | 4/2008 |
| WO | 2009003575 | 1/2009 |

* cited by examiner

INSTRUMENT FOR FUSING AND SEVERING TISSUE

CROSS REFERENCE TO RELATED APPLICATIONS

This patent application claims the benefit of European Patent Application No. EP 12173329.9 filed Jun. 25, 2012, the contents of which are incorporated herein by reference in its entirety.

TECHNICAL FIELD

The invention relates to an instrument for clamping off, closing and severing tissue or vessels, in particular blood vessels, on the living body of a human or animal patient.

BACKGROUND

In principle, instruments for closing and severing blood vessels have been known. One example can be learned from publication DE 602 26 015 T2.

Such instruments comprise an elongated shaft with a tool having two branches for clamping off a blood vessel, said tool being arranged on the distal end of said instrument. In addition, a knife that can be slid back and forth in longitudinal direction is arranged there in order to be able to sever a grasped and coagulated vessel. A handle with actuating means is provided on the proximal end of the shaft, by means of which the branches can be closed and the knife actuated. The branches are configured as electrodes in order to be able to heat the vessel clamped between them and to be able to fuse the vessel walls by coagulation.

When blood vessels are being severed it must be ensured that the ends of the severed vessel remain reliably closed. To accomplish this, additional requirements must be satisfied. For example, damage of the surrounding tissue is to be avoided. Closure of the vessel should be achievable largely independently of the size of the vessel and of the thickness of the vessel walls. In doing so, the confined space conditions must also be taken into consideration, said conditions requiring attention at the latest when the instrument is to be endoscopically or laparoscopically inserted.

Considering this, it is the object of the invention to provide an instrument for fusing and severing vessels, said instrument allowing the high-quality closing and severing of vessels.

SUMMARY

An example of the instrument in accordance with the invention is disposed for closing and severing blood vessels. It comprises two branches, at least one of these being supported so as to be preferably pivotable relative to the other. Both branches may be supported so as to be pivotable relative to the shaft. It is also possible for one of the branches to be rigidly connected to the shaft while the other is movably supported. Presently, the latter is preferred. The bearings of the branches may be configured in such a manner that non-uniform tissue can be grasped easily.

The first branch preferably comprises a base body consisting of an electrically insulating plastic material, for example ceramic or also another suitable synthetic material, said base body having a groove-like recess for an electrode and a guide slit for a knife. The groove-like recess may be adapted to the shape of the electrode. Preferably, the electrode has a concave recess. For example, this recess is configured as a cylindrical shell. However, said electrode may also have a U-shaped cross-section with straight limbs. Also, alternatively, said electrode may be configured as a flat electrode. Preferably, it is formed by a thin-walled sheet metal part that is imparted with the necessary mechanical stability by being supported in the base body.

Via an electrical connecting means, the electrode is connected to a line extending through the shaft. Preferably, the connecting means is an insulated electrical conductor. It passes through suitable channels or passages of the base body and may extend along the outside of the base body, for example, in particular in the vicinity of a joint where the second branch is movably supported on the first branch. To do so, the base body may be provided with a longitudinally extending recess in which the line is arranged. Consequently, it can be ensured that the head of the instrument will not exceed a maximum external diameter and that the instrument can be pushed through a trocar, e.g., for laparoscopic use.

Preferably, the electrical conductor that is used is a physiologically tolerable material such as silver, titanium or the like. The conductor may be embodied as a solid round wire, hollow wire, flat wire, flexible cord, ribbon or the like.

The knife is precisely guided, in view of its advance direction. In doing so, the knife is preferably guided centered to the electrode and also centered to the second branch, whereby it can move into the longitudinal slit of said second branch. During its advance, the knife may be guided—at least in part—by the longitudinal slit of the second branch.

Due to the precise guiding of the knife it can be ensured that the cut when a vessel is being severed can be placed centered in the previously fused region of the vessel. In doing so, both ends of the ultimately severed vessel have fused sections of equal length. The risk of potential, uncontrolled bleeding due to an imprecisely centered cut is minimized.

In accordance with one approach to the invention, the instrument comprises a vertical adjustment mechanism that is associated with the knife. This mechanism effects a movement of the knife as a function of the longitudinal movement of said knife perpendicular to said movement. This movement occurs perpendicular to the electrode and is thus referred to as the "vertical movement", independent of the absolute spatial orientation. Due to the vertical movement of the knife superimposing the longitudinal movement, the tip of the knife and its adjoining sliding edge are treated with care. The tip is only lowered onto the electrode that preferably consists of metal when the tip (and preferably also the adjoining cutting edge) has traversed sections, steps, joints or the like consisting of, e.g., ceramic and being located ahead of the electrode in view of the longitudinal movement. The tip and the cutting edge of the knife are thus guided in a contactless manner toward one end of the electrode and then set onto the electrode. A premature blunting of the cutting edge and/or the tip are avoided as a result of this. This ensures a clean cut of the tissue or vessel that is to be severed.

Preferably, the vertical adjustment mechanism comprises a cam surface arranged, e.g., on the base body, said cam surface being associated with a cam follower surface. The latter is connected to the knife or a knife carrier. The orientation of the surfaces is diagonal with respect to the direction of movement. As a result of this, the two surfaces derive the desired vertical adjustment movement from the longitudinal movement of the knife. Preferably, the distance of the cam follower surface from the sliding edge end is at least as great as the distance of the cam surface from the joint or step. As a result of this, the knife is safely guided over the step.

Preferably, the knife comprises a guide bead and a blade that are permanently connected to one another. Preferably, the guide bead is a longitudinal element extending in the direction of movement of the knife, for example, in the form of a rail of plastic material. The latter may be connected to a blade of metal. However, the blade may also consist of ceramic, diamond, plastic or another material. Alternatively, the guide bead may consist of a metal. It is also possible to configure the guide bead as a thickened region provided on the blade, so that the guide bead and the blade are designed in one piece without seams. However, the two-part design is preferred.

The lateral play of the knife in the guide slit and/or in the longitudinal slit is preferably less than five times the thickness D of the blade. Preferably, the lateral play of the knife is at most approximately the same as the thickness of the blade. As a result of this, it is possible to achieve the precisely centered guiding of the knife and thus a centered cut in the fused tissue region. The knife can be laterally guided by the guide slit. Alternatively, the knife can be laterally guided by the longitudinal slit. Preferably, the guide slit, as well as the longitudinal slit, provide lateral guiding.

Lateral play of the knife is understood to mean the distance of the flanks of the guide bead from the flank of the guide slit or the longitudinal slit with the knife in centered position. Consequently, the lateral movability of the knife corresponds to double the play.

Preferably, the knife has a straight sliding edge facing the electrode and adjoining said electrode. The sliding edge may be relatively short and preferably directly adjoins the cutting edge of the knife. Consequently, it is ensured that the vessel grasped between the branches is cut across its entire cross-section and that no remaining tissue remains unsevered.

Preferably, the cutting edge is arranged on the end side of the knife. Preferably, this end side is at an angle with respect to the direction of movement of the knife. This angle may be an acute angle. Preferably, the cutting edge is straight and extends toward the guide bead. Preferably, the guide bead projects beyond the cutting edge in order to prevent any part of the vessel that is to be severed from being forced over the knife and thus from not being cut.

The second branch has an electrically conductive surface—at least on its side facing the electrode. If the second branch consists of a non-metallic material, this surface may be a thin sheet-metal electrode. Preferably, however, the second branch is of solid metal. Independently thereof, the second branch has, on its side facing the electrode, a shape that follows the form of the electrode. In other words: A distance gap having an essentially constant gap width or a gap width that decreases toward the center is formed between the electrode and the second branch. Independently thereof, the surface of the second branch may be provided with a profile, e.g., with ribs, burls, or structures of another shape. The electrode may also be provided with a surface profile. Even if the profiles of the electrode and of the second branch are optionally different, they preferably have matching basic contours in order to define a distance gap having a gap width that preferably decreases toward the center.

The holding means for the fixation of the electrode on the first branch are preferably provided on the upper, oppositely located edges of the recess. Preferably, these holding means consist of electrically insulating projections that, e.g., consist of the material of the base body. Preferably, they extend in the direction toward the second branch and thus cover the upper edge of the electrode. Preferably, the projections define a gap having a distance B with respect to the second branch while the instrument is closed, said distance B being at least as great as the width A of the distance gap in the vicinity of the holding means.

The tissue of the vessel that is to be clamped off, said tissue not being coagulated here due to the electrically insulating properties of the projections, is grasped between the second branch and those projections. However, the tissue can be safely grasped even if the branches do not close symmetrically due to the properties of the tissue. For example, if a vessel having a cross-section that changes over its length is grasped, this can cause the lateral distances B to have different values, i.e., they are not identical. Nevertheless, the vessel is held securely. A slipping of the vessel is reliably precluded even if the tissue grasped between the branch and the electrode shrinks due to thermal action and coagulation, and the clamping force decreases at this site. A lateral slipping of the vessel and thus a later severing of the vessel at an unsuitable site with the subsequent actuation of the knife is reliably precluded in this manner.

For example, the holding means formed by the projections have a dual function: They hold the electrode and they improve the holding of the vessel.

Preferably, a spacing means is provided between the first and the second branches. This spacing means prevents the second branch from contacting the electrode and thus causing a short circuit. In addition, the spacing means prevents that too great a pressure is inadvertently applied to the vessel and that the vessel is thus crushed. Preferably, the spacing means consists of a metallic projection that is associated with a non-metallic abutment on the opposite side. Preferably, the metallic projection is electrically charged, i.e., connected to the electrode or to the second branch. As a result of this, errors that could occur when biological tissue gets between the projection and its associate abutment surface are avoided. Due to the application of an electrical current it is possible—in particular if the projection is located in the vicinity of the counterpole electrode—to introduce a certain current flow into the grasped biological tissue so that said tissue will shrink and no longer impair the adjustment of the desired minimum distance between the second branch and the electrode. Considering an alternative exemplary embodiment, it is possible to make the spacing means of an electrically non-conductive material. As a result of this, the risk of a short circuit between the branches can be reduced. In addition, this allows an expansion of the coagulation region.

BRIEF DESCRIPTION OF THE DRAWINGS

Additional details of advantageous embodiments of the invention can be inferred based on the description hereinafter, the dependent claims or the drawings.

DETAILED DESCRIPTION

Figures 1, 2, 3, 4:
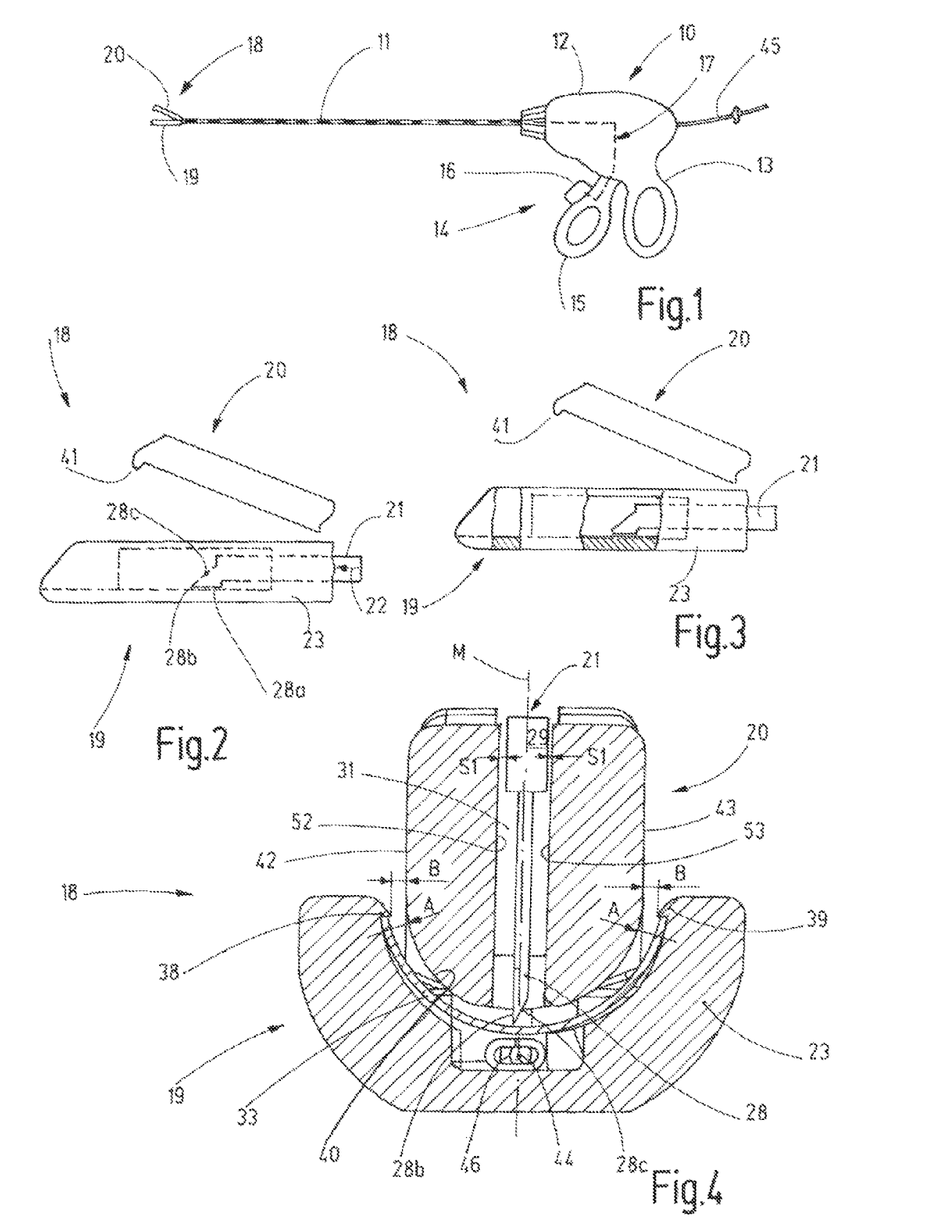
FIG. 1 comprises a schematized representation of an instrument in accordance with the invention.
FIG. 2 comprises a schematized side view of the branches and the knife of the instrument.
FIG. 3 comprises a general view, partially in section, of the branches and the knife in accordance with FIG. 2.
FIG. 4 comprises a simplified schematized representation in vertical section, viewed in the direction of the longitudinal axis, of the branches and the knife, with the tool closed.

FIG. 1 shows an instrument 10 that can be used for clamping off, fusing and severing a vessel, e.g., a blood vessel, during surgery on a human or animal body. In particular, the instrument 10 is disposed for endoscopic surgery. It comprises a slim shaft 11 that is held, on its proximal end, on a housing 12. Said housing comprises a handling means, for example, a handle 13, as well as actuating elements 14. Said actuating elements may comprise, e.g., a pivotable grip part 15 and/or an actuating button or lever 16 as well as, optionally, additional elements, e.g., electrical switches. The actuating elements 14 are connected to the application part 18 via force transmission means 17 that are only schematically indicated in dashed lines in FIG. 1, said application part being arranged on the distal end of the shaft 11. This application part or head 18 of the surgical instrument comprises at least the elements shown in FIGS. 2 and 3, namely a first branch 19, a second branch 20 and a knife 21. The branches 19, 20 are disposed for clamping off a vessel in that they are moved toward each other and firmly clamp the vessel between them. The knife 21 is disposed for severing the vessel.

In the present exemplary embodiment, the branch 19 is rigidly connected with the shaft 11, whereas the branch 20 can be pivoted toward and away from the branch 19 by actuating the grip part 15. As opposed to this, the knife 21 is pushed forward by actuating an actuating element, for example the grip part 15, in longitudinal direction of the shaft 11, as is indicated by arrow 22 in FIG. 2.

Figures 5, 6:
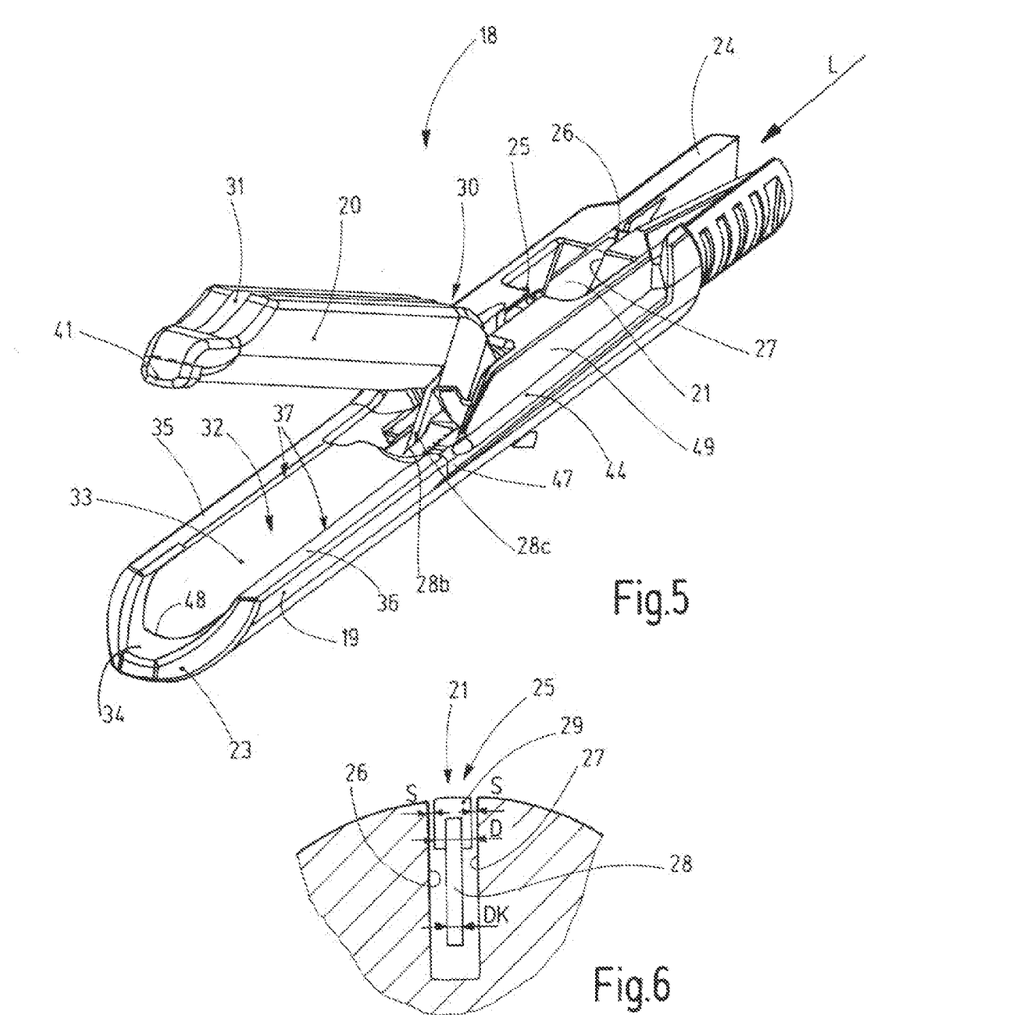
FIG. 5 comprises a perspective view of the head of the instrument in accordance with the invention.
FIG. 6 comprises a simplified schematized representation, in vertical section, viewed in the direction of the longitudinal axis, of the base body and the knife.

The branch 19 is composed of several parts. It comprises, e.g., a base body 23 consisting of a plastic material or of ceramic, as is particularly obvious from FIG. 4. On its shaft-side end, the base body 23 is rigidly connected to the shaft 11, said shaft comprising an extension 24 for this, as shown in FIG. 5. The elongated base body 23 extends away from said extension, said base body initially comprising a guide slit 25 for the knife 21. The guide slit 25 extending in longitudinal direction L through the elongated base body 23 has two slit flanks 26, 27, said flanks being parallel opposite each other at a distance and guiding a knife 21 between them. This is shown, in particular, by FIG. 6. In doing so, the knife 21, when in center position, is at a distance defined as play S from each slit flank 26, 27, said distance preferably being at most as large as the thickness D of the knife 21.

Said knife comprises a blade 28 that has a guide bead 29 on its upper edge. In this case D is defined as the thickness of the guide bead 29 (FIG. 6). The thickness DK is defined as the thickness of the blade 28. Preferably, the play S is at most five times the thickness DK. In the better case the thickness DK is at most double the play S. In other words: The knife may move back and forth at most by a measure of two times S between the flanks 26, 27. In the ideal case the thickness DK is at most equal to the play S.

Preferably, the knife 21 has a sliding edge 28a, e.g., on the blade 28, said sliding edge being able to slide on an electrode 33 of the branch 19 and guiding the height of the knife 21 (FIG. 2). As a result of this, the tip 28b of the blade 28 (FIGS. 4 and 5) adjoining the cutting edge 28c at the bottom can move—without wearing—on the electrode 33 or at an extremely small distance from said electrode.

In straight extension of the guide slit 25, there is an adjoining bearing or hinge region 30 in which the second branch 20 is pivotally supported on the base body 23. The branch 20 is connected to the force transmission means 17 that is not specifically shown in FIG. 5 in order to be pivoted by said means about an axis extending transversely to the base body 23.

The guide slit 25 continues as the longitudinal slit 31 through the branch 20. The longitudinal slit 31 is open—at least in downward direction—i.e., downward toward the base body 23. Preferably, its width corresponds at least approximately to the width of the guide slit 25. The slit flanks 52, 52 of the longitudinal slit 31 are plane surfaces that are oriented parallel to each other. With the knife 21, they define the dimensions of play S1, to which apply correspondingly what has been said hereinabove regarding the play S.

Below the branch 20, the base body 23 has a groove-like or indentation-like recess 32 in which the electrode 33 is arranged. In the present exemplary embodiment, the electrode 33 is a thin cylindrical shell of sheet metal. On the side facing the branch 19, said electrode has a curved, preferably concave, preferably closed, smooth surface. In doing so, the electrode 33 extends almost along the entire length of the recess 32, however, it leaves free a region 34 located on the front end of the base body 23. Holding means 37 are provided on the upper edges 35, 36 of the base body 23. As is shown by FIG. 4, said holding means are detent projections 38, 39 that consist of electrically insulating material and preferably are an integral component of the base body 23. The detent projections 38, 39 form locking lugs that extend over the upper edge of the electrode 33. Preferably, their length slightly exceeds the thickness of the electrode 33 so that they slightly extend beyond the exposed electrode surface of said electrode.

On its side facing the underside of the electrode 33, the upper branch 20 has an electrode surface 40 following the shape of the electrode 33. If the electrode 33 has the shape of a cylindrical shell, for example, the electrode surface 40 also follows a circular arc, wherein said circular arc has a slightly smaller radius. Independent of this basic shape, the electrode 33, as well as the electrode surface 40, may have local deviations in the form of recesses, projections, burls, ribs or the like.

On the distal end of the second branch 20 there is a lug-like projection 41 extending toward the base body 23, said projection abutting against the end-side region 34 of the base body 23 when the instrument is closed. In this state, a distance gap having the width A is defined between the electrode surface 40 and the interior side of the electrode 33. Preferably, this width A is at least minimally greater than the distance B between the projections 38 and 39, respectively, and the electrode surface 40 or the adjoining flank 42, 43 of the branch 20.

As is obvious from FIGS. 4 and 5, the electrode 33 is connected to a power source via an electrical conductor 44. In doing so, the conductor 44 extends through the shaft 11, first into the housing 12, then to a not specifically shown switch located therein and, optionally, to a supply device via a feed line 45.

Likewise, a not specifically shown conductor leads from the branch 20 to the device. The conductor 44 may be a round wire or the like provided with an insulation 46, for example. It is connected to the electrode 33 approximately centered at a location between the electrode 33 and the base body 23. In particular in the hinge region 30, the conductor 44 is passed through a lateral opening 47 of the base body 23 on the outside of said base body and extends there in a longitudinal recess 49 up to the extension 24. There, the conductor 44 again enters the shaft 11. Specifically, the conductor 44 may be an insulated silver wire.

The knife 21 is associated with a vertical adjustment mechanism 54 that is disposed to impart the knife 21 with a movement occurring perpendicularly toward or away from the electrode 33. This movement occurs transversely (perpendicularly in FIGS. 7 through 11) with respect to the longitudinal movement of the knife 21 occurring along the longitudinal direction L. The vertical adjustment mechanism 54 is disposed to derive a vertical adjustment movement from the longitudinal movement of the knife 21. The vertical adjustment mechanism 54 holds the knife 21, when it is in its retracting position in accordance with FIG. 7, in a lifted position in which its tip 28b and its sliding edge 28a—as shown by FIG. 11—are lifted far enough off the electrode 33 that even a step 55 adjoining one end of the electrode 33 will not be contacted.

Figure 10:
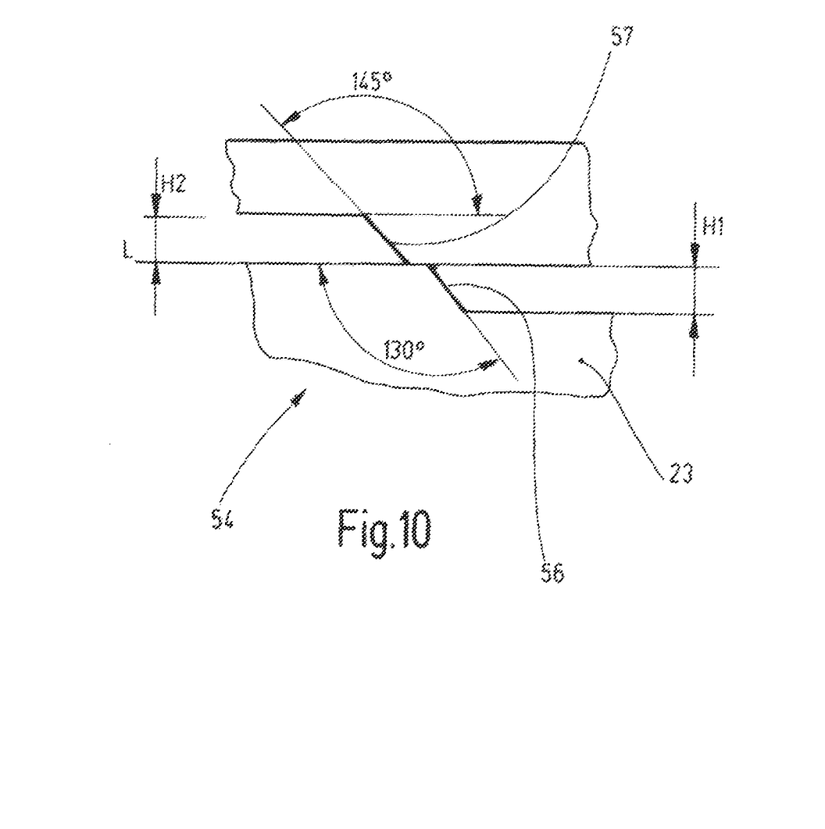
FIG. 10 comprises a schematic representation of a vertical adjustment mechanism for the knife.
Figure 11:
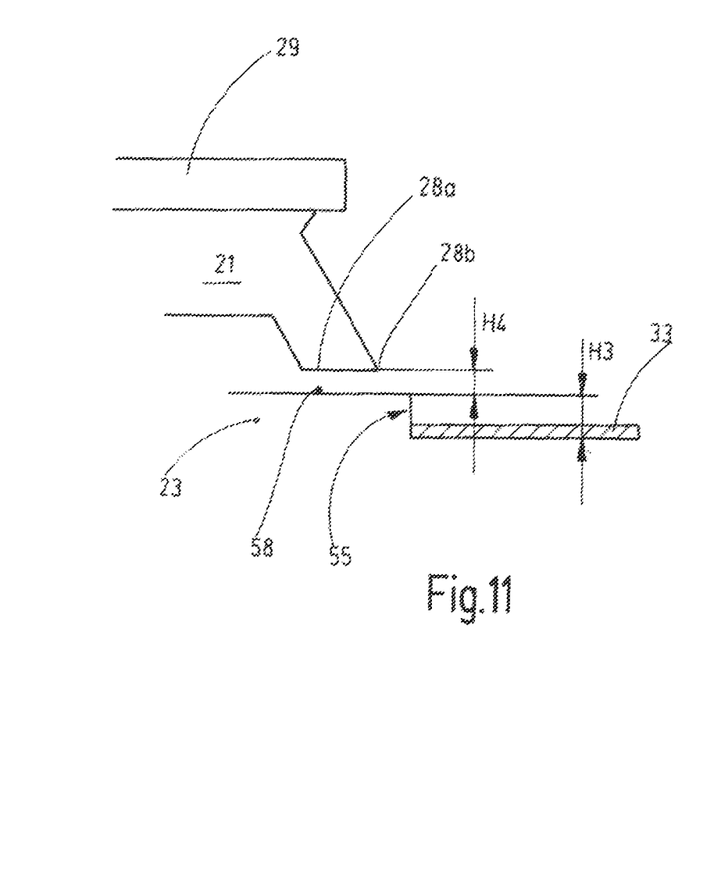
FIG. 11 comprises a lateral schematic view of the knife in inoperative position and the associate electrode.

FIG. 10 shows the vertical adjustment mechanism 54 by itself. The latter comprises a cam surface 56 that may be provided, e.g., on the base body 23, on the extension 24 or on a part that is rigidly connected to the base body 23, and comprises a cam follower surface 57 that is provided on the knife 21 or on a part that is rigidly connected therewith. The cam surface 56 and the cam follower surface 57 may be flat surfaces or also differently configured surfaces—for example, when viewed from the side—they may be S-shaped or arcuately curved surfaces. Irrespective of their specific form, they are oriented obliquely with respect to the longitudinal direction L. As is indicated by FIG. 10, for example, an angle of 130 degrees relative to the longitudinal direction L is suitable. The cam follower surface 57 may be inclined at the same angle or also at a different angle with respect to the longitudinal direction L. For example, an angle of 145 degrees is suitable. Other angles are possible. The cam surface 56 is oriented transversely with respect to the longitudinal direction L and preferably has a height H1 of 0.4 mm, for example. Preferably, measured transversely with respect to the longitudinal direction L, the cam follower surface 57 has a height H2 of 0.5 mm, for example. Preferably, the height H1 is clearly greater than the height H3 of the step 55, as can be inferred from FIG. 11. For example, the height H3 may be 0.2 mm. In doing so, a minimum distance H4 of the tip 28b and the sliding edge 28a from the surface 58 adjoining the step 55 of 0.1 mm to 0.2 mm, for example, is maintained.

The instrument 10 described so far operates as follows:

For closing and severing a vessel, said vessel is grasped between the branches 19, 20. By actuating the grip part 15, the branches 19, 20 are moved toward each other so that the vessel is clamped off and the vessel walls are pressed against each other. In doing so, the vessel walls are compressed, in particular, between the electrode surface 40 and the electrode 33. In addition, said vessels are grasped between the projections 38, 39 and the electrode surface 40 or the flanks 42, 43. In the ideal case, the projection 41 is seated on the region 34 of the base body 23, said projection acting as an abutment, and thus prevents the vessel from being crushed.

By applying an electrical current or voltage between the branch 20 and the electrode 33, preferably an RF voltage, a coagulation process is initiated, in the course of which the cells of the vessel walls are opened and protein is released and denatured. The vessel walls that are pressed against each other between the branch 20 and the electrode 33 will stick together. In doing so, the vessel walls can lose volume. Independently of the contraction of the volume of the vessel walls, however, the vessels grasped between the projections 38, 39 and the branch 20 remain—at least to a great extent—in natural state and thus are subject to hardly any contraction. They remain securely grasped, thus preventing a lateral slippage of the vessel. This is of importance, in particular, when relatively small vessels are closed.

If, however, a remainder of tissue has ended up between the projection 41 and the region 34 acting as the abutment so that the gap width A is slightly greater than actually intended, again, the narrow gap B acts as a safety against a lateral slippage of the vessel. In addition, the distance between the projection 41 and the front end 48 of the electrode 33 may be so small that tissue present there will coagulate and thus contract. Also, this again aids the secure grasping of the tissue between the branches 19, 20.

Once the coagulation process has sufficiently progressed, the surgeon can actuate the knife 21 by actuating the grip part 15, for example. Now, starting with the position as in FIG. 7, the knife is guided centered in the guide slit 25 and the longitudinal slit 31 and pushed in longitudinal direction L toward the free end of the branches 19, 20. In doing so, the knife 21 moves more or less precisely in the center plane M, said plane being indicated in a chain line in FIG. 4. This ensures that equally long regions of closed vessel ends are formed on both sides of the knife 21. The risk of an off-center cut and thus the risk of uncontrolled bleeding is thus minimized.

Figure 7:
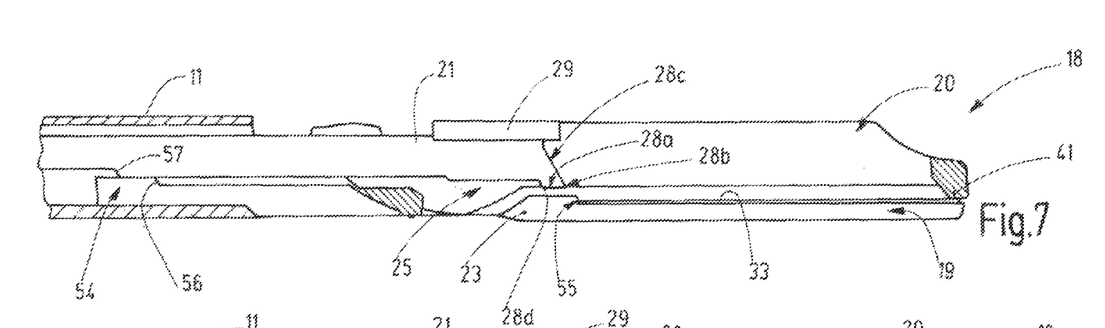
FIGS. 7-9 comprise representations, in longitudinal section, of the head of the inventive instrument in accordance with FIG. 5, in three different positions of the knife.
Figure 8:
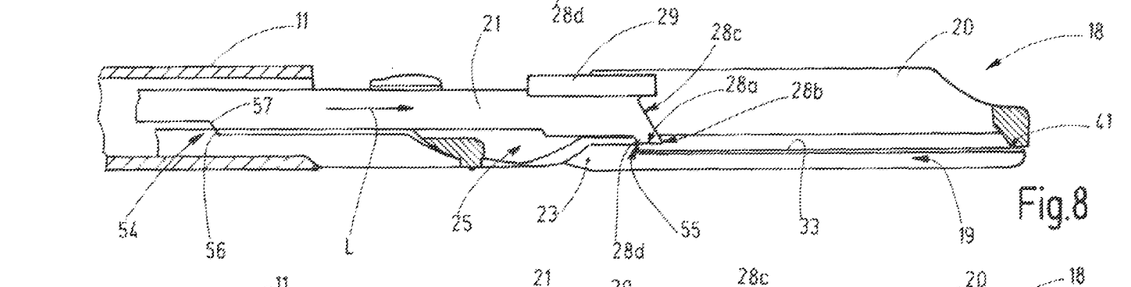
Figure 9:
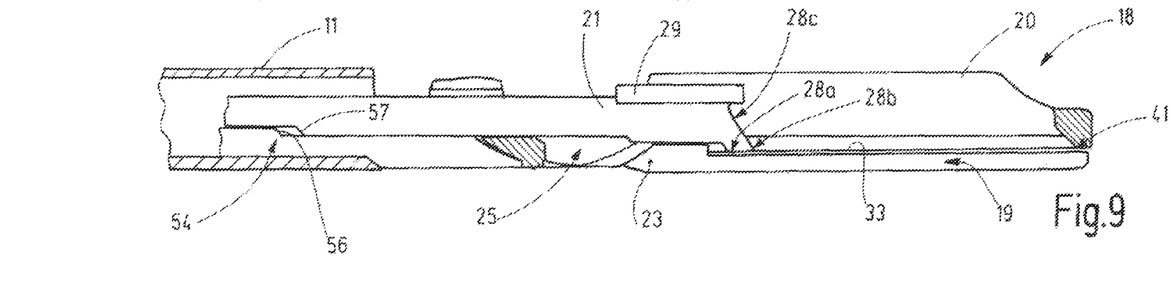

In inoperative position in accordance with FIG. 7, the tip 28a of the knife 21 is initially positioned behind the step 55—viewed from the electrode 33—at which step the base body 23 consisting of ceramic or another material adjoins the electrode 33 at a joint. In doing so, the distance of the rear (left side in FIG. 7) end 28d of the sliding edge 28a from the step 55 is slightly smaller than the distance between the cam surface 56 and the cam follower surface 57. The position of the sliding edge 28a in accordance with FIG. 7 is shown separately in FIG. 11. As the knife 21 is advanced more, it reaches the position as in FIG. 8. Shortly after the end 28d distal to the tip has passed the step 55, the cam follower surface 57 comes into abutment with the cam surface 56. Now, there will be a lowering or closing movement in the course of which the knife 21 is moved toward the electrode 33 in a direction transverse to the longitudinal direction L. In doing so, the knife 21 is somewhat pretensioned toward the electrode 33 because of the elasticity of its not specifically illustrated holder or because of the force transmission means 17. Now the sliding edge 28a is set onto the electrode 33, as shown by FIG. 9. During the continued advance, the cutting edge 28c can sever the grasped and coagulated vessel.

The sliding edge 28a is lifted when the knife 21 is retracted, this occurring correspondingly in reverse order. In any event, the sliding edge 28a, like the tip 28b, is spared contact with potentially more abrasive materials, for example ceramic parts, so that the sharpness of the tip 28b remains maintained. This ensures that a high cutting quality can be achieved even after extended use.

An instrument 10 preferably suitable for minimally invasive surgery, e.g., an instrument that can be inserted through a trocar into a body, comprises two branches 19, 20 for clamping off vessels and a centrally guided knife 21. Due to the centered guidance of the knife in at least one of the branches 19, 20, disadvantages are avoided, such disadvantages potentially otherwise occurring as a result of the off-center severing of the coagulated tissue. In addition, wear is reduced due to the clean, centered guiding of the knife 21. Consequently, the invention makes possible a better cutting quality and a longer service life of the knife 21.

One of the branches preferably comprises a ceramic base body 23 which has inward extending projections 38, 39 formed on its upper edges, said projections having the form of an undercut. These electrically insulating projections extend in the direction toward the center plane M and provide two improvements: On the one hand, the assembly of the electrode 33 is facilitated considerably. On the other hand, two tissue tension sites are created. The projections may be configured in such a manner that—with the branches 20, 19 closed—the distance A between the electrode formed by the upper branch 20 and the electrode 33, at the point where the distance A has its greatest width, and the two distances B between the projections 38, 39 and the branch 20 are the same, almost the same or minimally smaller than the distance A. This has the advantage that, during the coagulation process during which the tissue volume in the coagulation region decreases, the tissue is nevertheless held securely. Preferably, starting from the projections 38, 39, the distance A tapers toward the guide slit 31. Referring to the present instrument, the coagulation width is determined by the insulating projections 38, 39 and can thus be reliably reproduced. This considerably improves the coagulation quality.

An instrument 10 for fusing and severing vessels in accordance with the invention comprises a first branch 19 with a first electrode 33 and a second branch 20 that is supported so as to be movable toward and away from the first electrode 33, wherein the second branch 20 has a longitudinal slit 31. A knife 21 is arranged in said slit so as to be movable longitudinally relative to the shaft 11. The knife 21 is associated with a vertical adjustment mechanism 54 for adjusting the knife 21 perpendicularly to the longitudinal movement as a function of the longitudinal movement of said knife. As a result of this, a premature dulling of the tip 28b or the sliding edge 28a of the knife 21 due to contact with the ceramic base body or the edges or the step 55 is avoided.

LIST OF REFERENCE SIGNS

10 Instrument
11 Shaft
12 Housing
13 Handle
14 Actuating elements
15 Grip part
16 Actuating button or lever
17 Force transmission means
18 Application part, head
19 First branch
20 Second branch
21 Knife
22 Arrow
23 Base body
24 Extension
25 Guide slit
L Longitudinal direction and advance direction
26, 27 Slit flanks
S Play between 25 and 21
D Thickness of the knife 21
DK Thickness of the blade 28
28 Blade
28a Sliding edge
28b Tip
28c Cutting edge
28d End of the sliding edge 28a distal to the tip
29 Guide bead
30 Hinge region
31 Longitudinal slit
S1 Play between 31 and 21
32 Recess
33 Electrode
34 End-side region of the base body 23
35, 36 Upper edges
37 Holding means
38, 39 Detent projections
40 Electrode surface
41 Projection
A Width of the distance gap between 33 and 40
B Distance between 38, 39 and 40
42, 43 Flank of the branch 20
44 Conductor
45 Feed line
46 Insulation
47 Lateral opening of the base body 23
48 Front end of 33
M Center plane
49 Longitudinal recess
52, 53 Slit flanks of 31
54 Vertical adjustment mechanism
55 Step
56 Cam surface
57 Cam follower surface
H1 Height of cam surface 56 and hence adjustment path
H2 Height of the cam follower surface 57
H3 Height of the step 55
H4 Distance between the sliding edge 28a and the surface 58
58 Surface

What is claimed is:

1. Instrument (10) for fusing and severing vessels, the instrument comprising:
    an elongated shaft (11) extending away from a housing (12),
    a first branch (19) with a first electrode (33) and having a step (55) at an end of the first electrode (33),
    a second branch (20) that is supported so as to be movable toward and away from the first electrode (33), wherein the second branch (20) has a longitudinal slit (31),
    a knife (21) that is arranged so as to be movable with a longitudinal movement along the shaft (11) and arranged so as to extend into or be movable into the longitudinal slit (31),
    wherein the knife (21) is associated with a vertical adjustment mechanism (54) for adjusting the knife (21) perpendicularly to the longitudinal movement as a function of the longitudinal movement of said knife;
    wherein the vertical adjustment mechanism (54) comprises a cam surface (56) arranged stationarily relative to the shaft (11) and with a cam follower surface (57) arranged stationarily relative to the knife (21); and
    wherein the vertical adjustment mechanism (54) defines an adjustment path (H1) that is greater than a height (H3) of the step (55) such that the knife's cutting edge moves in a contactless manner longitudinally toward the first electrode before moving vertically toward the first electrode.

2. Instrument as in claim 1, wherein the first branch (19) comprises an electrically insulating base body (23) having a groove-like recess (32) and a guide slit (25), wherein holding means (37, 38, 39) for stationarily supporting the first electrode (33) are arranged on the base body (23), said electrode being curved.

3. Instrument as in claim 2, wherein the step (55) is formed between the electrode (33) and the base body (23).

4. Instrument as in claim 3, wherein the knife (21) has a straight, longitudinally extending sliding edge (28a) facing the first electrode (33) and abutting against said electrode, said sliding edge extending from a sliding edge tip (28b) to a sliding edge end (28d);
    wherein a distance of the cam follower surface (57) from the sliding edge end (28d) is at least as great as the distance of the cam surface (56) from the step (55).

5. Instrument as in claim 1, wherein the vertical adjustment mechanism (54) is disposed to move the knife (21), during a first advance movement directed along the first electrode (33), perpendicularly toward the first electrode and, during a retraction movement directed along the first electrode, perpendicularly to the retraction movement away from the first electrode (33).

6. Instrument as in claim 1, wherein the vertical adjustment mechanism (54) is configured to bias an end (28d) of a sliding edge (28a) distal to a tip of the knife against a step (55) in the vicinity of the first electrode (33).

7. Instrument as in claim 1, wherein the knife (21) has a straight, longitudinally extending sliding edge (28a) facing the first electrode (33) and abutting against said electrode, said sliding edge extending from a sliding edge tip (28b) to a sliding edge end (28d).

8. Instrument as in claim 1, wherein the cam surface (56) and the cam follower surface (57) are surfaces that are oriented obliquely with respect to an advance direction (L).

9. Instrument as in claim 1, wherein the knife (21) has an end-side cutting edge (28c) that is oriented at an angle relative to the direction of movement of the knife (21).

10. Instrument as in claim 1, wherein the second branch (20) is configured as a solid metal body.

11. Instrument as in claim 1, wherein the second branch (20) has, on its side facing the electrode (33) of the first branch (19), a form following the form of the electrode (33).

12. Instrument as in claim 1, wherein with the branches (19, 20) of the instrument (10) closed, a distance gap having a width (A) is defined between the electrode (33) and the second branch (20).

13. Instrument as in claim 1, wherein holding means (37) are provided on both opposing edges (35, 36) of the recess (32).

14. Instrument as in claim 1 wherein the vertical adjustment mechanism is separate from the step and located between the handle and the step.

15. A method of operation of an instrument, the method comprising:
   moving a knife along a shaft extending from a housing, the shaft including a first branch with an electrode and having a step on an end of the electrode and a second branch that defines a longitudinal slit such that the knife moves with a longitudinal movement into the longitudinal slit;
   moving the knife with a vertical adjustment mechanism comprising a cam surface arranged stationarily relative to the shaft and a cam follower surface arranged stationarily relative to the knife to adjust the knife perpendicularly to the longitudinal movement as a function of the longitudinal movement of the knife wherein the knife moves with a perpendicular component of an adjustment path (H1) that is greater than a height (H3) of the step such that the knife's cutting edge moves in a contactless manner longitudinally toward the first electrode before moving vertically toward the first electrode.

16. The method of claim 15 further comprising the vertical adjustment mechanism moving the knife, during a first advance movement, directed along the first electrode, perpendicularly toward the first electrode and, during a retraction movement, directed along the first electrode, perpendicularly to the retraction movement away from the first electrode.

17. The method of claim 15 further comprising the vertical adjustment mechanism biasing an end of a sliding edge distal to a tip of the knife against the step in the vicinity of the first electrode.

18. The method of claim 15 wherein the vertical adjustment mechanism is separate from the step and located between the handle and the step.

19. Instrument (10) for fusing and severing vessels, the instrument comprising:
   an elongated shaft (11) extending away from a housing (12),
   a first branch (19) with a first electrode (33),
   a second branch (20) that is supported so as to be movable toward and away from the first electrode (33), wherein the second branch (20) has a longitudinal slit (31),
   a knife (21) that is arranged so as to be movable with a longitudinal movement along the shaft (11) and arranged so as to extend into or be movable into the longitudinal slit (31),
   wherein the knife (21) is associated with a vertical adjustment mechanism (54) configured to adjust the knife (21) perpendicularly to the longitudinal movement as a function of the longitudinal movement of said knife such that the knife's cutting edge moves in a contactless manner longitudinally toward the first electrode before moving vertically toward the first electrode;
   wherein the vertical adjustment mechanism (54) comprises a cam surface (56) arranged stationarily relative to the shaft (11) and with a cam follower surface (57) separate from and arranged stationarily relative to the knife's (21) cutting edge.

20. Instrument as in claim 19 wherein the vertical adjustment mechanism is separate from the step and located between the handle and the step.

* * * * *